United States Patent [19]
Gold et al.

[11] 4,303,490
[45] * Dec. 1, 1981

[54] EXHAUST ELECTRODE PROCESS FOR EXHAUST GAS OXYGEN SENSOR

[75] Inventors: Terry J. Gold, Flint; Frederick L. Kennard, III, Holly; Paul C. Kikuchi; Ralph V. Wilhelm, Jr., both of Flint, all of Mich.

[73] Assignee: General Motors Corporation, Detroit, Mich.

[ * ] Notice: The portion of the term of this patent subsequent to Jan. 13, 1998, has been disclaimed.

[21] Appl. No.: 189,732

[22] Filed: Sep. 22, 1980

Related U.S. Application Data

[63] Continuation-in-part of Ser. No. 89,264, Oct. 29, 1979, Pat. No. 4,244,798, which is a continuation-in-part of Ser. No. 30,775, Apr. 17, 1979, abandoned.

[51] Int. Cl.$^3$ .............................................. C23C 15/00
[52] U.S. Cl. .......................... 204/192 C; 204/192 SP; 204/195 S
[58] Field of Search ........... 204/192 C, 192 SP, 195 S

[56] References Cited

U.S. PATENT DOCUMENTS

| | | | |
|---|---|---|---|
| 3,844,920 | 10/1974 | Burgett et al. | 204/195 S |
| 3,978,006 | 8/1976 | Topp et al. | 252/477 R |
| 4,021,326 | 3/1977 | Pollner et al. | 204/195 S |
| 4,116,883 | 9/1978 | Rhodes | 252/463 |
| 4,129,848 | 12/1978 | Frank et al. | 338/308 |
| 4,136,000 | 1/1979 | Davis et al. | 204/195 S |

*Primary Examiner*—Delbert E. Gantz
*Assistant Examiner*—William Leader
*Attorney, Agent, or Firm*—Robert J. Wallace

[57] ABSTRACT

A method of sputtering a palladium or palladium-platinum exhaust gas electrode onto a vitrified zirconia thimble for an electrochemical-type exhaust gas oxygen sensor. Porous high surface area films are deposited that have more consistent properties. A sputtering target is spaced about 3.0-4.5 cm from the thimble and more than 6 cm from the sputtering anode. A pressure of about 10-20 millitorr is used during sputtering at a DC power of about 13-22 watts/cm$^2$ of target area.

3 Claims, No Drawings

EXHAUST ELECTRODE PROCESS FOR EXHAUST GAS OXYGEN SENSOR

RELATED PATENT APPLICATION

This patent application is a continuation-in-part of U.S. patent application Ser. No. 089,264, filed Oct. 29, 1979 and entitled "Exhaust Electrode Process for Exhaust Gas Oxygen Sensor", now U.S. Pat. No. 4,244,798. The latter is, in turn, a continuation-in-part of U.S. patent application Ser. No. 030,775, filed Apr. 17, 1979 and also entitled "Exhaust Electrode Process for Exhaust Gas Oxygen Sensor," now abandoned.

FIELD OF THE INVENTION

This invention relates to solid electrolyte, electrochemical-type exhaust gas oxygen sensors. It more particularly relates to a sputtering process for depositing a palladium and/or a palladium-platinum exhaust electrode onto vitrified zirconia thimbles for such sensors.

BACKGROUND OF THE INVENTION

A typical automotive-type solid electrolyte exhaust gas oxygen sensor is disclosed in U.S. Pat. No. 3,844,920 Burgett et al. It has a zirconia sensing element shaped as a tapered thimble. One end is open and has a circumferential flange. The other end is closed, and forms the most active part of the element. The interior and exterior of the thimble have separate porous electrode coatings of platinum, palladium, or the like. The inner electrode is exposed to a source of oxygen, such as air or a mixed metal oxide, for establishing a reference potential. This electrode has generally been formed by painting a coating of a platinum ink onto the zirconia thimble, drying the coating, and then firing the coated thimble at an elevated temperature. An improved technique by which it can be applied is described and claimed in U.S. patent application Ser. No. 080,449 entitled "Reference Electrode Printing Process and Mask for Exhaust Gas Oxygen Sensor," filed on Oct. 1, 1979 in the name of John Trevorrow and assigned to the assignee of this invention, now U.S. Pat. No. 4,264,647.

The outer electrode is exposed to the exhaust gas for establishing a potential determined by exhaust gas oxygen concentration. The outer electrode can be a porous precious metal thick film, like the inner electrode. However, it is preferred that this outer electrode be a thin film, applied by evaporation, sputtering, chemical vapor deposition or other such thin film deposition techniques. On the other hand, it has been difficult to consistently reproduce desirable properties, such as porosity and electrical parameters, in the thin film electrodes. As a result, yields of satisfactory electrode properties have been limited, and various ancillary procedures have been developed to improve them. For example, U.S. Pat. No. 3,978,006 Topp et al. discloses heating the solid electrolyte body after electrode deposition, to form pores in the electrode coating if it is not porous as deposited. U.S. Pat. No. 4,136,000 Davis et al. discloses treating the electroded sensor element chemically and electrolytically to enhance sensor properties. Moreover, it is known that zirconia-type exhaust gas sensors, particularly those with a sputtered exhaust gas electrode, are likely to change electrical characteristics after a short time in operation. Generally the change is an improvement, such as a reduction in switching response time. Consequently, it has been proposed to operate such sensors functionally in an actual or simulated exhaust gas stream until they are sufficiently stabilized, before installing them in an actual working system. Such treatments, of course, add to the cost of manufacture. Moreover, the yield of higher performance sensors is still inherently limited by the quality of the electrode film originally deposited.

We have found how to sputter palladium and palladium-platinum films onto the zirconia surface in such a manner that the film is consistently porous as deposited and has a consistently high surface area as deposited, which contributes to a greater yield of high quality sensors. Sensors with low lean-to-rich switching response times are produced, without post-electroding treatments. Palladium electrodes made in accordance with this invention consistently do not appear to exhibit any significant initial use changes, which have been referred to as break-in or aging effects. For example, pure palladium electrodes sputtered by this invention can exhibit rich-to-lean switching response times that are initially about as low as the lean-to-rich switching response times. Hence, palladium electrodes produced by our process have more symmetrical switching response times, as formed. With a significant proportion of platinum included in the electrode, the rich-to-lean switching response of the electrode made by this invention may be low, as formed, but not as low as the lean-to-rich switching response until after a short actual or simulated aging. Hence, a high yield of significantly fast sensors is obtained, as formed, or with only minimal aging. In fact, if sensors having exhaust electrodes produced in accordance with this invention are susceptible to aging, it can probably be done by a simple furnace treatment, as is disclosed and claimed in U.S. patent application Ser. No. 30,747 entitled "Aging Treatment for Exhaust Gas Oxygen Sensor," filed on April 17, 1979 in the names of Morris Berg, Slater W. Hawes, Frederick L. Kennard, III and Paul C. Kikuchi and assigned to the assignee hereof, now U.S. Pat. No. 4,253,934.

OBJECTS AND SUMMARY OF THE INVENTION

An object of this invention is to provide an improved sputtering process for depositing a palladium or palladium-platinum exhaust electrode onto a zirconia solid electrolyte body for an electrochemical-type exhaust gas oxygen sensor.

The invention is an improvement over parent U.S. Ser. No. 89,264, U.S. Pat. No. 4,244,798, in that it comprehends sputtering palladium-platinum, as well as onto a vitrified zirconia solid electrolyte body which is widely spaced from a sputtering target. The target is more than about 3.7 centimeters away from the workpiece, in a preferred example. The palladium containing metal is DC sputtered from the unusually distant target under a relatively high pressure of about 10–20 millitorr and a sputtering power of about 13–22 watts/cm$^2$ of target area.

DESCRIPTION OF THE PREFERRED EMBODIMENTS

Vitrified zirconia thimbles the same as described in the aforementioned U.S. patent application Ser. No. 80,449, U.S. Pat. No. 4,264,647, can be exteriorly coated in accordance with this invention. These thimbles are about 3–5 cm long and are of zirconia partially or fully stabilized in its cubic form by the inclusion of about 4–8 mole percent yttria. Each thimble has a taper on its outer surface of about 3 degrees—38 minutes. In a particular example, it has an axis length of about 3.66 cm. Its wider end has a circumferential shoulder and a diameter about 0.82 cm immediately below the shoulder. Its narrower end is closed and rounded, having an external spherical radius of curvature of about 3 mm. Its diameter adjacent the rounded end is about 0.4 cm. We believe it is important to control deposition on and near the rounded end tip. This appears to be the most active part of the sensing element. The inner electrode is formed on the thimbles first. We prefer it to be a platinum ink thick film fired to the zirconia surface, and preferably applied by the coating process described in the aforementioned U.S. Ser. No. 80,449, U.S. Pat. No. 4,264,647. The thimbles are then cleaned to receive the thin film outer exhaust electrode in accordance with this invention.

As is usual for any thin film deposition process, the zirconia surface should be well cleaned before depositing the outer electrode onto it in accordance with this invention. We expect that any normal and accepted high quality cleaning procedures can be used. In our parent U.S. Ser. No. 89,264, U.S. Pat. No. 4,244,798, we describe a cleaning procedure that includes ultrasonically degreasing the zirconia with freon, and then heating it to about 600° C. in air for about an hour. The zirconia thimbles are then placed on a stainless steel pallet, and the pallet placed in a vacuum chamber of a sputtering apparatus such as a model MRC902 DC magnetron sputtering apparatus obtained from Materials Research Corporation of Orangeburg, N.Y. This apparatus has an elongated but fairly shallow vacuum chamber with provision for two fixed targets disposed over a single anode that is much larger than the targets. An antechamber at one end of the vacuum chamber contains an elevator mechanism, and serves as a load lock for the vacuum chamber. More specific details on this particular apparatus and its use are contained in U.S. Ser. No. 98,726, entitled "Electrode Sputtering Process for Exhaust Gas Oxygen Sensor," and filed Nov. 30, 1979 in the names of Terry J. Gold, Kurt D. Humphrey, Keith A. Penney, Robert J. Smith, Randy L. Voto, and Ralph V. Wilhelm, Jr., now U.S. Pat. No. 4,253,931.

The vacuum chamber is pumped down to a pressure of approximately 100 millitorr. The chamber is then immediately pumped down to a pressure below $2 \times 10^{-6}$ torr. A flow of argon at about 75–100 cc per minute is then started through the vacuum chamber while pumping continues. The flow of argon and the pumping continues and the vacuum valving is adjusted until pressure equilibrates at about 10–20 millitorr. This argon pressure is similarly dynamically maintained during the sputtering process. Chamber atmosphere is thus continually refreshed during sputtering.

In our process of U.S. Ser. No. 89,264, U.S. Pat. No. 4,244,798 and of this patent application, we can simultaneously sputter electrode films onto large groups of such zirconia thimbles such as over 200 thimbles. The pallet with its thimbles is placed directly on a horizontal planar steel pallet carrier. The thimble axes are parallel to each other and oriented vertically. Their open ends rest on the pallet. The pallet carrier is disposed about 0.5–1.5 cm above the anode. However, we do not know if any separation is needed at all. The thimble closed ends face upwardly toward a planar target surface of a cathode, which surface is spaced about 3.8 cm above the thimble closed ends. In our aforementioned U.S. Ser. No. 89,264, U.S. Pat. No. 4,244,798 the sputtering target is preferably a platinum sheet bonded to a supporting copper backing plate. In the subject patent application, the target is preferably a palladium or palladium-platinum alloy sheet, bonded to a supporting copper backing plate. On the other hand, if a laminated deposit is desired, separate such palladium and platinum targets may be used, as will hereinafter be described more fully. In any event, the target is assembled with a cathode that includes water cooling means and a magnet array. An argon pressure of 10–20 millitorr is dynamically maintained in the sputtering chamber. A DC voltage of approximately 500 to 800 is applied between the target and the anode. The sputtering power supply is adjusted to provide a DC power between the target and the anode of approximately 13–22 watts/cm$^2$ of target area. No special means are used in the pallet, pallet carrier, or anode to heat or cool the thimbles during sputtering.

Sputtering is continued under the above conditions, while maintaining the aforementioned 10–20 millitorr argon pressure, until a palladium or palladium-platinum weight of about 5–10 mg is deposited onto each element. For pure platinum, a 10 mg deposit will produce a porous crystalline catalytic film about 1.0–1.5 micrometers thick on the rounded end, about 0.65–1.0 micrometers thick about 0.5 cm back from that end, and about 0.3–0.75 micrometers thick about 2 cm back from the rounded end. We believe that a palladium weight that is one-half to two times the previously mentioned platinum weight can be used. The lighter palladium weight is preferred for performance and cost savings but heavier coatings may provide better resistance to poisoning and the like. 5 mg of palladium produce a thickness about equal to 10 mg of platinum. The weights for palladium-platinum combinations should be approximately adjusted to obtain equivalent thicknesses. For 7–13 mg of pure platinum, a sputtering time in argon of about 3–5 minutes is preferred. For 5–10 mg of pure palladium, a sputtering time in argon of about 2–4 minutes is preferred. We believe that electrode porosity and perhaps surface area, and the resultant sensor electrical characteristics are a function of electrode thickness. Also, the temperature to which the ceramic self-heats during deposition is apparently important.

The techniques of this invention should provide an apparent electrode surface area at least double its geometric surface area. By apparent surface areas, we mean the surface area in the film coated part of the element as determined by conventional gas adsorption techniques. By geometric surface area, we mean surface area as determined from a drawing of the element. In many instances the process of this invention will provide a twofold increase in apparent surface area as deposited over the underlying zirconia surface, if the latter is not particularly rough. Adhesion of the sputtered film to its underlying zirconia can be increased by heating the electroded element in air for about 1 hour at 800° C. Such a heating of a palladium film opens large pores in the film, about 0.2–2 micrometers in width. The number and size of these openings appear to depend on the time and temperature of heating and the thickness of the film. This heating does not seem to be significantly detrimental to sensor performance. On the other hand, it seems important that the film have a high porosity and surface area as deposited. Otherwise, sensor performance is adversely affected by this heating.

The electrode film is then preferably given a porous ceramic coating on all its parts except where electrical connection is to be made. The porous ceramic coating can be catalytic or noncatalytic, as desired, without significant initial operating effects on the resultant sensor. For example, it can be a gamma alumina coating prepared and applied as disclosed in U.S. Pat. No. 4,116,883 Rhodes. However, we prefer to flame spray a magnesium-aluminate spinel coating onto the electrode film after the heat treatment to increase electrode adhesion. We recognize that applying the porous overcoating by flame spraying can apparently significantly physically alter the electrode film. However, it nonetheless appears that the essential functional characteristics of the electrode film remain substantially unchanged by the flame spraying. Consequently, the as-deposited characteristics of the electrode film remain fundamentally important.

As previously mentioned, the sputtering target, or cathode, is spaced at least about 3.5-4.0, preferably about 3.8 cm above the closed ends of the zirconia thimbles and about 7.6 cm above the anode. This larger than the normal spacing is believed to provide improved electrode porosity and better process controllability. The preferred spacing appears to be critical. If a spacing closer than about 3.0 cm is used between the zirconia closed ends and the target, less porous films appear to result. A spacing greater than about 4.5 cm appears unnecessary and objectionable. It requires higher power settings and argon pressures to obtain a satisfactory coating rate. Deposition in unwanted areas of the apparatus is more likely to occur. Still further, the characteristics of the electrode film are less likely to be reproducible.

The platinum sputtering process of our aforementioned U.S. Ser. No. 89,264, Pat. No. 4,244,798, is also applicable not just to pure palladium and pure platinum. It is also applicable to palladium-platinum alloys, and to palladium-platinum laminates. Electrodes consisting essentially of pure palladium can be produced that are not only fast but quite symmetrical in switching response times as formed. For example, in batches of well over 200 thimbles electroded with palladium in accordance with our invention, 80% of the sensors in a batch will usually have rich-to-lean and lean-to-rich switching response times, as formed, that are below about 160 ms and 80 ms, respectively, at 700° F. A large proportion of these sensors will even have rich-to-lean and lean-to-rich switching response times, respectively, less than about 100 ms and 60 ms, as formed.

Fastest and most symmetrical palladium electrodes have been obtained on the aforementioned thimbles with electrode weights of about 5-10 mg. For comparison, we prefer to use electrode weights of about 7-13 mg for platinum. For alloys and laminates of palladium and platinum, intermediate weights, i.e. thicknesses, would presumably be preferred, depending on the sensor characteristics required and the costs involved. The palladium-to-platinum ratio in the electrodes can correspondingly vary from chiefly palladium to chiefly platinum.

If platinum and palladium metal are both to be present in the electrode, they can be combined in various ways. For example, the electrode could be a palladium-platinum alloy. If so, the target can be made of a palladium-platinum alloy of the electrode composition desired. On the other hand, it may be desirable to initially sputter a substantially pure palladium coating onto the thimble, and then cover it with a substantially pure platinum coating, or vice versa. In the alternative, multiple layers of each may be desired, with or without a subsequent heat treatment to partially or completely interdiffuse them. In such instance, one could use a sputtering apparatus having two targets in the same sputtering chamber, with one target being of palladium and the other target being of platinum. Any desired number of layers and ratio of layer thicknesses can obviously be obtained by merely appropriately switching from one target to the other, with no significant change in sputtering conditions. On the other hand, when sputtering a predominantly platinum layer one may choose to switch to a sputtering atmosphere having a major proportion of nitrogen and/or oxygen, as will hereinafter be described in connection with U.S. Ser. No. 98,726, U.S. Pat. No. 4,253,931.

The nature of the sputtering target, or targets, is no more critical to this invention than it is to any other sputtering of palladium, platinum, or alloys thereof. The target can be obtained from any commercial source, and the metal sheet it comprises is preferably a high purity. However, we recognize that in some instances it may prove to be desirable to include minor amounts of other metals than palladium and/or platinum in the target along with the pure palladium, pure platinum, or pure alloys thereof as for example, a few percent, up to about 5 percent of rhodium. Thus, we contemplate the target to consist essentially of palladium, platinum, or alloys of the two, and prefer it to be of at least substantially pure such metals or alloys. Because of the cost, we prefer a target in which the metal being sputtered is only a surface coating.

A power setting of at least about 13 watts/cm$^2$ of target area is required. Lesser power settings apparently result in deposition rates too slow to produce significant porosity and surface area. Conversely, power settings in excess of about 22 watts/cm$^2$ of target area seem to be too severe on system components. Also, the higher power settings may produce platinum deposition in unwanted areas within the vacuum chamber. In any event sensor performance is less reproducible with less than about 13 watts/cm$^2$ of target area. We have found that pressures of about 10-20 millitorr are preferred. This higher pressure range is preferred even though higher power settings are employed. At pressures less than 10 millitorr, the coating appears to be less porous, perhaps because the rate of deposition is too low. Thus, if a cathode-magnet assembly is used that permits maximum deposition rate at less than about 10 millitorr, we would expect similar porous films at lower pressures. At pressures above about 20 millitorr, deposition rate also decreases. Also, deposition may begin to occur on unwanted areas within the vacuum chamber.

The sputtering conditions hereinbefore described provide improved electrodes as deposited. For example, substantially pure platinum electrodes having lean-to-rich switching response times of less than 600 milliseconds can be consistently produced under commercial production conditions. Rich-to-lean switching response times of less than 1200 milliseconds are consistently produced, as deposited. However, after only a relatively short functioning of an hour or so in exhaust gas the rich-to-lean switching response times of such platinum electrodes consistently drop below 600 milliseconds. Controllability is at about 15 parts air to 1 part fuel, i.e. on the lean side and within about 0.5 air/fuel ratios. Thus, even if the sensor is not fast as formed, it can be consistently operationally aged to provide a fast-acting sensor. Further, the sensor characteristics obtained using substantially pure platinum electrodes produced by our process are more reproducible. Higher yields of fast-acting sensors can be obtained by functional aging.

In addition, it has also been discovered that a simple furnace treatment in nitrogen can artificially age sensors having platinum electrodes made in accordance with our process. The furnace treatment is described and claimed in the aforementioned U.S. patent application Ser. No. 30,747, U.S. Pat. No. 4,253,934. DC magnetron sputtering is disclosed herein. However, the principles of this invention should also be applicable to ordinary DC sputtering and to RF sputtering. Still further, the electrode of this invention may be more durable if a platinum cermet stripe is first applied to the outer zirconia surface and fired. If narrow, the stripe need not be porous, and can be of any commercially available platinum ink that adheres well to zirconia when fired, and to which the sputtered platinum deposited over it will adhere.

High yield of platinum electrodes that are fast as formed are obtained if the platinum is sputtered under an atmosphere predominantly of nitrogen and/or oxygen. U.S. Ser. No. 98,726, filed Nov. 30, 1979, entitled "Electrode Sputtering Process for Exhaust Gas Oxygen Sensor," T. J. Gold et al., now U.S. Pat. No. 4,253,931, describes the benefits of sputtering platinum in an atmosphere about 65–75% by volume nitrogen and/or oxygen and the balance argon. High yields of substantially pure platinum electrodes can be obtained that are quite fast as formed. If the sensors from such batches are also given the aforementioned U.S. Ser. No. 30,747, U.S. Pat. No. 4,253,934, nitrogen furnace treatment, the yields of fast sensors increase even further. On the other hand, we have found that the nitrogen and/or oxygen atmosphere during substantially pure palladium deposition does not provide any analogous advantage. Similarly, the nitrogen furnace treatment of finished sensors that is contemplated by the aforementioned U.S. Ser. No. 30,747, U.S. Pat. No. 4,253,934, provides no known benefit on the pure palladium electrodes of this invention. Palladium electrodes produced by this invention are fast as deposited. As to palladium-platinum combinations, nitrogen and/or oxygen sputtering atmospheres and/or nitrogen furnace post-electroding treatments may be desirable but probably only for high platinum content electrodes. Analogously, if palladium and platinum are to be successively sputtered, one may choose to use a nitrogen sputtering atmosphere for both the platinum and the palladium, for convenience.

The embodiments of the invention in which an exclusive property or privilege is claimed are defined as follows:

1. In a method of sputtering an electrode of at least one metal selected from the group consisting of platinum and palladium onto a vitrified zirconia solid electrolyte body for an electrochemical-type exhaust gas oxygen sensor, the improvement wherein a target of at least one metal selected from the group consisting of platinum and palladium spaced at least about 3.0 cm from the body is used in the sputtering, the metal is sputtered at a pressure of about 10–20 millitorr, and a sputtering power of about 13–22 watts/cm$^2$ of target area is used, whereby the electrode is porous as deposited and has an apparent surface area at least double the geometric area of the zirconia surface on which it lies.

2. In a method of sputtering a palladium exhaust gas electrode onto a vitrified zirconia thimble for an electrochemical-type exhaust gas oxygen sensor, the improvement wherein a generally planar target consisting essentially of palladium is oriented normal to the axis of the zirconia thimble and spaced about 3.0–4.5 cm from a closed end on the thimble, the palladium is sputtered using an atmosphere having a pressure of approximately 10–20 millitorr and a DC power of about 13–22 watts/cm$^2$ of target area, whereby the palladium electrode is consistently and reproducibly porous as deposited and forms a sensor electrode having a generally symmetrical switching response time.

3. In a method of sputtering a palladium exhaust gas electrode onto a vitrified zirconia thimble for an electrochemical-type exhaust gas oxygen sensor, the improvement wherein the thimble is about 3–5 cm long, a target having a generally planar surface consisting essentially of palladium is oriented normal to the thimble axis and spaced about 3.5–4.0 cm from a closed end on the thimble, the palladium is DC magnetron sputtered in an argon atmosphere having a pressure of approximately 10–20 millitorr and a DC power of about 13–22 watts/cm$^2$ of target area and for a duration to produce an electrode thickness of about 1.0–1.5 micrometer on said end and about 0.65–1.0 micrometer on thimble side walls about 0.5 cm back from that end, whereby the palladium electrode is porous as deposited and has an apparent surface area as deposited at least double its geometric surface area.

* * * * *